(12) United States Patent
DeTar

(10) Patent No.: US 11,753,430 B2
(45) Date of Patent: Sep. 12, 2023

(54) METHOD OF MAKING COBALT COMPOUNDS FOR FEED SUPPLEMENTS

(71) Applicant: Vitalix, Inc., Sidney, NE (US)

(72) Inventor: Marvin B. DeTar, Wickliffe, OH (US)

(73) Assignee: Vitalix, Inc., Sidney, NE (US)

( * ) Notice: Subject to any disclaimer, the term of this patent is extended or adjusted under 35 U.S.C. 154(b) by 0 days.

(21) Appl. No.: 17/307,095

(22) Filed: May 4, 2021

(65) Prior Publication Data

US 2021/0380621 A1 Dec. 9, 2021

(51) Int. Cl.
| | |
|---|---|
| *C07F 15/06* | (2006.01) |
| *A23K 20/105* | (2016.01) |
| *B01D 9/00* | (2006.01) |
| *B01D 1/22* | (2006.01) |

(52) U.S. Cl.
CPC .......... *C07F 15/065* (2013.01); *A23K 20/105* (2016.05); *B01D 1/22* (2013.01); *B01D 9/0004* (2013.01); *B01D 9/0045* (2013.01); *B01D 9/0081* (2013.01)

(58) Field of Classification Search
CPC ...... A23K 20/105; A23K 50/10; C07F 15/065
See application file for complete search history.

(56) References Cited

U.S. PATENT DOCUMENTS

| | | |
|---|---|---|
| 3,133,942 A | 5/1964 | Hahl |
| 3,198,635 A | 8/1965 | Anderson |
| 4,009,263 A | 2/1977 | Shafer |
| 4,060,535 A | 11/1977 | Cinco |
| RE32,909 E | 4/1989 | Lionelle et al. |
| 5,591,878 A | 1/1997 | Nelson et al. |
| 5,622,739 A | 4/1997 | Benton et al. |
| 5,707,679 A | 1/1998 | Nelson |
| 5,795,615 A | 8/1998 | Nelson et al. |
| 7,495,117 B2 | 2/2009 | Goh et al. |
| 8,182,573 B2 | 5/2012 | Stark et al. |
| 8,575,212 B2 | 11/2013 | Knochenmus et al. |
| 9,663,438 B2 | 5/2017 | Reddy |
| 10,265,340 B2 | 4/2019 | LeBrun et al. |
| 2014/0611875 | 1/2014 | Knochenmus et al. |
| 2021/0015120 A1* | 1/2021 | Lamb ................... A23K 20/105 |

* cited by examiner

*Primary Examiner* — Pancham Bakshi
(74) *Attorney, Agent, or Firm* — Ancel W. Lewis, Jr.; Cochran Freund & Young LLC

(57) ABSTRACT

A method of making a cobalt compound for feed supplements includes the steps of dissolving cobalt acetate tetrahydrate in water to form a mixture, adding an acid to the mixture, sonicating the mixture for a selected time, removing acetic acid from the mixture, and separating crystals of the cobalt compound from the mixture.

20 Claims, No Drawings

METHOD OF MAKING COBALT COMPOUNDS FOR FEED SUPPLEMENTS

TECHNICAL FIELD

The present invention relates to feed supplements, and more particularly to a method of making cobalt compounds for feed supplements.

BACKGROUND ART

Cobalt is a component of Vitamin $B_{12}$. Vitamin $B_{12}$ is produced in ruminant animals by microorganisms in the rumen. Cobalt can be provided in feed supplements for livestock, such as cattle, goats and sheep, to prevent Vitamin $B_{12}$ deficiency.

Most cobalt compounds cannot be used in feed supplements. Some cobalt compounds, such as cobalt metal and dicobalt carbonyl are toxic. Cobalt carbonate has been used as a feed supplement for many years, but a significant portion of it is not taken up easily by many of the microorganisms in the rumen. Cobalt chloride releases hydrogen chloride which can deactivate enzymes and is an irritant on the tongue. Cobalt oxide and cobalt hydroxide are very insoluble at physiological temperatures and are not useful in feed supplements.

Cobalt lactate, cobalt propionate, cobalt gluconate and cobalt heptogluconate can be used in feed supplements. The bioavailability of these compounds can be improved by increasing the relative surface area. Prior known methods for producing these compounds have required high temperatures, high magnetic fields or grinding the product of the chemical reaction.

DISCLOSURE OF THE INVENTION

A method of making a cobalt compound for feed supplements includes the steps of dissolving cobalt acetate tetrahydrate in water at a selected temperature to form a mixture, adding a selected acid to the mixture, sonicating the mixture for a selected time, removing acetic acid from the mixture, and separating crystals of the cobalt compound from the mixture. The method may include the step of stirring or rotating the mixture during the step of sonicating. The step of separating may also include the substep of precipitating the crystals from the mixture by cooling the mixture.

BRIEF DESCRIPTION OF THE DRAWINGS

Details of this invention are described in connection with the accompanying drawings that bear similar reference numerals in which:
No figures.

DETAILED DESCRIPTION OF THE INVENTION

A method of making a cobalt compound for feed supplements, embodying features of the present invention, includes the steps of dissolving cobalt acetate tetrahydrate in water at a selected temperature to form a mixture, adding a selected acid to the mixture, sonicating the mixture for a selected time, removing acetic acid from the mixture, and separating crystals of the cobalt compound from the mixture.

The selected acid can be any carboxylic acid. For feed supplements, lactic, propionic, gluconic and heptogloconic are used to produce cobalt lactate, cobalt propionate, cobalt gluconate and cobalt heptogluconate, respectively.

In the step of dissolving, the cobalt acetate tetrahydrate is dissolved in a minimum of water at between 55° C. and 70° C. The subsequent steps are modified depending on the pKa and boiling point of the selected acid. Acetic acid has a pKa of 4.75.

For acids such as lactic acid, citric acid, erythorbic acid and acids in general possessing a pKa lower by about 0.05 units than acetic acid, the step of adding includes dissolving the selected acid in a minimum of water at 55° C. and adding the selected acid so that the mole ratio of acid to cobalt is preferably 2.02 or more, more preferably 2.13 or more and most preferably 2.25 or more. After the step of adding, the method may include the step of stirring the mixture during the step of sonicating. The step of sonicating includes sonicating the mixture at about 0.25 watts/cm$^2$ at 20-55 KHz, or sufficient power that standing waves are clearly visible, for about one hour. The step of separating includes the substep of reducing the temperature to 17° C. or below, during the step of sonicating, to precipitate the crystals from the mixture. The step of separating can also include the substeps of filtering, washing with cold water to remove acetic acid and drying the crystals. The step of removing acetic acid from the mixture can include sparging with a wet stream of nitrogen at 55° C. or subjecting the mixture to thin film evaporation of acetic acid under reduced pressure or both.

For acids such as butyric, isobutyric, valeric, isovaleric and a variety of higher aliphatic acids and oleic, linolenic and linoleic acids, and acids in general possessing a pKa about equal to or higher than that of acetic acid, the step of adding includes adding the selected acid so that the mole ratio of acid to cobalt is 2.25 or more. The method can include the step of rapidly rotating the mixture during the step of sonicating. The step of sonicating includes sonicating the mixture at 55° C. at about 0.3 watts/cm$^2$ at 20-55 KHz. The step of removing acetic acid from the mixture can include subjecting the mixture to thin film evaporation of acetic acid under reduced pressure.

For propionic acid the mixture is kept below about 70° C. The step of adding includes adding the propionic acid so that the mole ratio of acid to cobalt is 3.0 or more. The method includes the step of rapidly rotating the mixture during the step of sonicating. The step of sonicating includes sonicating the mixture at 55° C. and at about 0.4 watts/cm$^2$ at 20-55 KHz. The step of removing acetic acid from the mixture includes slowly evacuating acetic acid at reduced pressure while adding 95% propionic acid as needed. The azeotrope of water and propionic acid boils at about 99° C. and acetic acid boils at about 117° C., at atmospheric pressure. Propionic acid boils at about 42° C. at 20 mm Hg, and acetic acid boils at about 17° C. at 10 mm Hg. The step of separating can also include vacuum drying the mixture. The temperature is kept below about 70° C. to prevent formation of sticky cobalt hydroxides.

The step of removing acetic acid can include blending the mixture into basic inorganic materials that then form acetate salts, primarily with calcium, magnesium, potassium or sodium ions. The step of separating can include containing the crystals in a slurry, suspension, or gel.

The method can also include a step of forming a premix, including the substeps of adding, after the step of dissolving, gluconic acid to provide an almost 1:1 premix mixture of cobalt acetate and cobalt gluconate compounds, and then sonicating the premix mixture. The premix remained in solution at 15° C. for over ten days. When additional gluconic acid (1.1 eq of total gluconic acid to acetic acid) was added, and gently mixed, within a half hour precipitation of very fine cobalt gluconate crystals occurred. This indicates that with the very low levels of water employed, this inorganic mixture retained a memory of its sonication. Without sonication, the cobalt gluconate crystals that formed exhibited less than 20 times the surface area observed with sonication.

Sonicating the mixture with ultrasonic frequencies causes pressure waves where molecules are jostled apart, promoting both the exchange of acetic acid to the selected acid and promoting formation of fine crystals. The method produces cobalt compounds for feed supplements without requiring high temperatures, high magnetic fields or grinding the product of the chemical reaction. The method produces fine crystals with a relatively high surface area and high bioavailability for the microorganisms in the rumen.

All of the ingredients have been designed to be reused. The acetic acid removed from the mixture can be reused. After the step of separating crystals of the cobalt compound from the mixture, the remaining mixture of cobalt compounds and the heavier carbon acids can be recycled into subsequent batches.

Although the present invention has been described with a certain degree of particularity, it is understood that the present disclosure has been made by way of example and that changes in details of structure may be made without departing from the spirit thereof.

What is claimed is:

1. A method of making a cobalt compound for feed supplements comprising the steps of:
    dissolving cobalt acetate tetrahydrate in a minimum of water at between 55° C. and 70° C. to form a mixture,
    adding a selected acid to said mixture,
    sonicating said mixture for a selected time,
    removing acetic acid from said mixture, and
    separating crystals of said cobalt compound from said mixture.

2. The method of making a cobalt compound as set forth in claim 1 wherein said selected acid is a carboxylic acid.

3. The method of making a cobalt compound as set forth in claim 1 wherein said selected acid is chosen from the group consisting of lactic acid, propionic acid, gluconic acid and heptogloconic acid.

4. The method of making a cobalt compound as set forth in claim 1 wherein said step of adding, for acids possessing a pKa lower by about 0.05 units than acetic acid, includes dissolving said selected acid in a minimum of water at 55° C. and adding said selected acid so that the mole ratio of acid to cobalt is more than 2.25.

5. The method of making a cobalt compound as set forth in claim 4 including the step of stirring said mixture during said step of sonicating.

6. The method of making a cobalt compound as set forth in claim 5 wherein said step of sonicating includes sonicating said mixture at about 0.25 watts/cm2 at 20-55 KHz for about one hour at a power setting sufficient to provide standing waves at 20-55 KHz for about one hour.

7. The method of making a cobalt compound as set forth in claim 6 wherein said step of separating includes the substep of cooling said mixture, during said step of sonicating, to precipitate said crystals from said mixture.

8. The method of making a cobalt compound as set forth in claim 7 wherein said substep of cooling includes reducing the temperature to below 17° C.

9. The method of making a cobalt compound as set forth in claim 8 wherein said step of separating includes the substeps of filtering, washing with cold water and drying said crystals.

10. The method of making a cobalt compound as set forth in claim 1 wherein said step of adding, for acids possessing a pKa higher than acetic acid, includes adding the selected acid so that the mole ratio of acid to cobalt is more than 2.25.

11. The method of making a cobalt compound as set forth in claim 10 including the step of rapidly rotating said mixture during said step of sonicating.

12. The method of making a cobalt compound as set forth in claim 11 wherein said step of sonicating includes sonicating said mixture at 55° C. at about 0.3 watts/cm2 at 20-55 KHz.

13. The method of making a cobalt compound as set forth in claim 12 wherein said step of removing acetic acid from said mixture includes subjecting said mixture to thin film evaporation of acetic acid under reduced pressure.

14. The method of making a cobalt compound as set forth in claim 1 wherein said step of adding, for propionic acid, includes adding said selected acid so that the mole ratio of acid to cobalt is more than 3.0.

15. The method of making a cobalt compound as set forth in claim 14 including the step of rapidly rotating said mixture during said step of sonicating.

16. The method of making a cobalt compound as set forth in claim 15 wherein said step of sonicating includes sonicating the mixture at 55° C. at about 0.4 watts/cm2 at 20-55 KHz.

17. The method of making a cobalt compound as set forth in claim 16 wherein said step of removing acetic acid from said mixture includes slowly evacuating acetic acid at reduced pressure while adding 95% propionic acid as needed.

18. The method of making a cobalt compound as set forth in claim 1 wherein said step of removing acetic acid includes blending said mixture into basic inorganic materials that then form acetate salts.

19. The method of making a cobalt compound as set forth in claim 1 including the step of forming a premix, including the substeps of adding, after said step of dissolving, gluconic acid to provide an almost 1:1 premix mixture of cobalt acetate and cobalt gluconate compounds, and then sonicating said premix mixture.

20. A method of making a cobalt compound for feed supplements comprising the steps of:
    dissolving cobalt acetate tetrahydrate in a minimum of water at between 55° C. and 70° C. to form a mixture,
    adding a selected acid to said mixture, wherein said selected acid is chosen from the group consisting of lactic acid, propionic acid, gluconic acid and heptogloconic acid,
    sonicating said mixture for a selected time,
    removing acetic acid from said mixture, and
    separating crystals of said cobalt compound from said mixture, including the substeps of cooling said mixture, during said step of sonicating, to precipitate said crystals from said mixture, filtering said crystals, washing said crystals with cold water and drying said crystals.

* * * * *